United States Patent [19]

Guiney

[11] 4,116,240
[45] Sep. 26, 1978

[54] MIXING SYRINGE

[76] Inventor: Aeneas C. Guiney, 2855 Silverhill, Pontiac, Mich. 48055

[21] Appl. No.: 776,528

[22] Filed: Mar. 11, 1977

[51] Int. Cl.² .............................................. A61M 5/00
[52] U.S. Cl. ............................... 128/218 M; 128/272.1
[58] Field of Search ........................ 128/218 M, 272.1

[56] References Cited

U.S. PATENT DOCUMENTS

| 2,305,278 | 12/1942 | Smith .............................. | 128/218 M |
| 2,869,543 | 1/1959 | Ratcliff et al. .................. | 128/218 M |
| 3,477,431 | 11/1969 | Walecka .......................... | 128/218 M |
| 3,477,432 | 11/1969 | Shaw ............................... | 128/218 M |
| 3,557,787 | 1/1971 | Cohen ............................. | 128/218 M |
| 3,885,710 | 5/1975 | Cohen ............................. | 128/218 M |

FOREIGN PATENT DOCUMENTS 1,791,293  12/1975  Fed. Rep. of Germany ...... 128/218 M Primary Examiner—John D. Yasko
Attorney, Agent, or Firm—Fisher, Gerhardt & Groh

[57] ABSTRACT

A single barrel mixing syringe in which one material such as a liquid is stored in the bore of the syringe barrel and another material such as a powder is stored in a chamber formed in a resilient piston head which forms not only the powder containing compartment but also the seals preventing leakage of liquid from the syringe. The two chambers are separated by a wall which may be displaced in one embodiment by differential pressure during movement of the piston portion of the syringe and in another embodiment by a separate plunger which displaces the wall.

4 Claims, 9 Drawing Figures

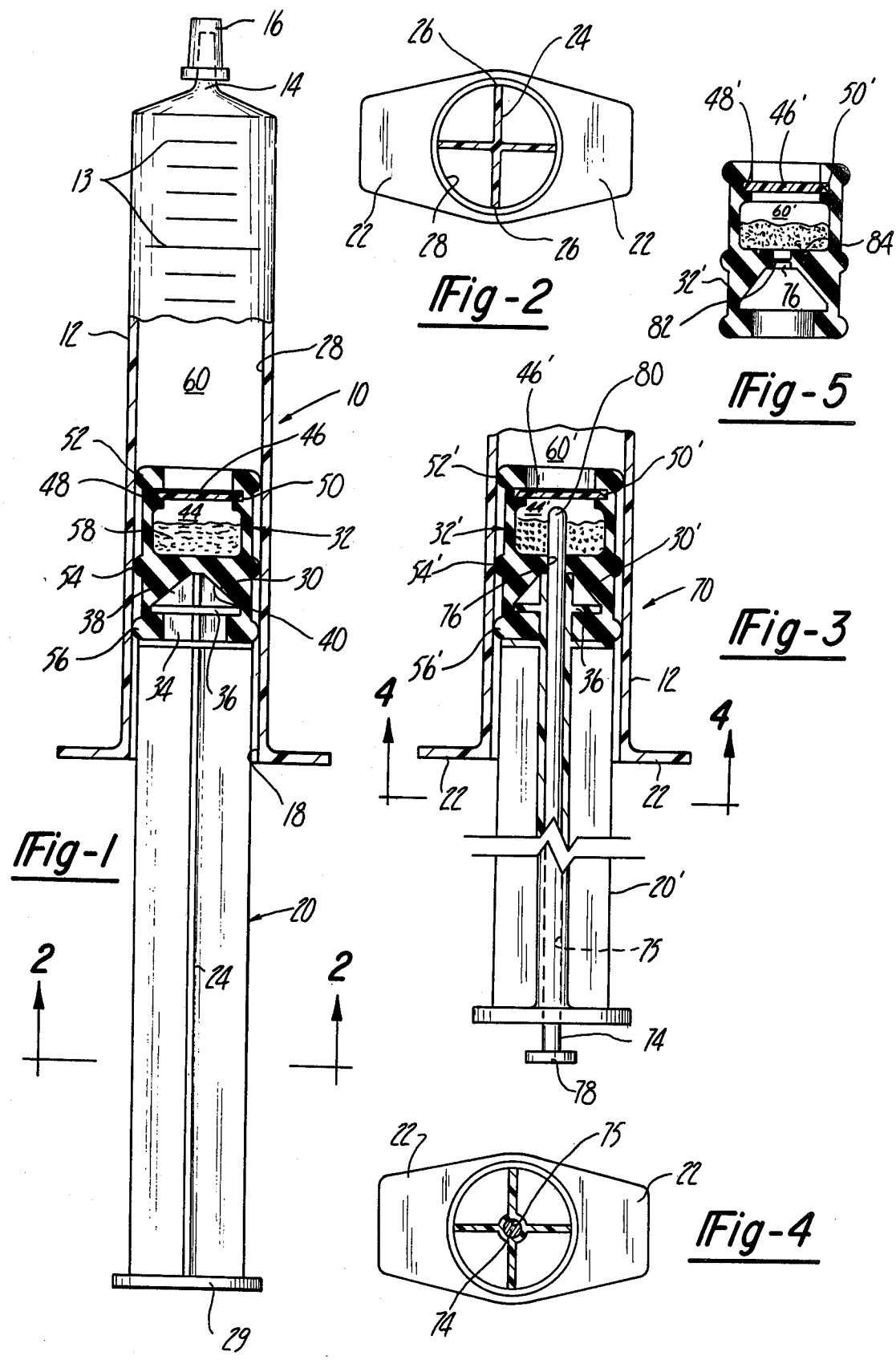

MIXING SYRINGE

This is a continuation-in-part application of my original application Ser. No. 693,423 filed June 7, 1976.

This invention relates to hypodermic syringes in which two materials are stored separately within the syringe until shortly before they are mixed together and ejected from the syringe.

Syringes for storing and mixing materials such as a powdered pharmaceutical or medication in one compartment and a diluent or solvent in another compartment are known. Prior to use, the diluent or solvent and the powdered material are mixed together internally of the syringe so that they may be ejected through a hypodermic needle or opening in the syringe.

Syringes of this type have taken many forms and have included syringes with telescoping barrels, plugs, frangible diaphragms and the like. For the most part many of these devices become very complex and are difficult to use without contaminating the materials being mixed.

It is an object of the invention to provide a single barrel hypodermic syringe in which materials may be stored separately for mixing together just prior to use.

Another object of the invention is to provide a syringe in which one of the materials may be premeasured and stored for insertion into a syringe at the time of use.

Still another object of the invention is to provide a single cylinder syringe in which accurately measured amounts of powdered material and liquid solvent can be stored completely separately from each other and which can be mixed without contamination just prior to use.

Still another object of the invention is to provide a mixing syringe of this type in which the entire operation may be carried out with one hand.

A syringe for storing two materials in separate chambers until shortly before the materials are mixed together for ejection from the syringe has been provided in which one chamber is formed within the barrel of the syringe itself and in which the other chamber for storing the other material is formed in a resilient piston head. The resilient piston head forms sealing portions to prevent liquid leakage and supports a movable wall which maintains the two materials separate. When the materials are to be mixed the wall is displaced in one embodiment of the invention by pressure differential acting on a wall during movement of the syringe plunger in the cylinder of the syringe. In another embodiment of the invention the wall separating the two materials is displaced by an auxiliary plunger. The two materials to be mixed and dispensed are maintained separately until just prior to use and if desired one of the materials stored in the chamber formed in the piston head may be stored separately from the remainder of the syringe until just prior to use.

FIG. 1 is a sectional view of the mixing syringe embodying the invention;

FIG. 2 is a cross-sectional view taken on line 2—2 in FIG. 1;

FIG. 3 is a sectional view of another embodiment of the invention;

FIG. 4 is a cross-sectional view taken generally on line 4—4 in FIG. 3;

FIG. 5 is a view of the piston head portion of the syringe before assembly in the syringe;

Figure 7:
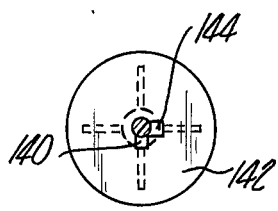
FIG. 7 is a view taken generally in the direction of line 7—7 in FIG. 6.

Referring to the drawings and particularly to FIG. 1, the mixing syringe embodying the invention is designated generally at 10. The syringe 10 includes a cylinder or barrel 12 which may be formed of glass but most practically can be formed from a transparent plastic material which not only is strong but also is inert to nearly all types of medication. The transparent cylinder is provided with indicia or graduations such as those designated at 13 for indicating the volume of liquid in the cylinder 12.

The cylinder 12 has a nipple or needle adapter 14 formed at one end which is adapted to fit a standard hypodermic needle. The needle adapter 14 is fitted with a protective cap 16 which may remain in place during storage of the syringe and which is removed at the time that the syringe is fitted with a hypodermic needle or other fitting, not shown, for conveying the liquid mixture from the mixing syringe 10.

One end of the cylinder 12 is open as indicated at 18 to slidably receive the plunger assembly 20. Adjacent the open end 18 of the tube 12, provision is made for radially outwardly extending and diametrically opposed flange portions 22 which serve as handles engaging the fingers of the user during operation of the syringe.

The plunger 20 is preferably made of a plastic material and includes longitudinally extending web portions 24 generally coextensive in length to the length of the cylinder 12. The longitudinal web portions 24 has a cross section in the form of a cross, as best seen in FIG. 2, so that the longitudinal extending edges slidably engage the internal walls of bore 28 to guide the plunger during its movement in the barrel 12. The exposed end of the plunger is provided with a thumb rest or pad 29.

The interior end of the plunger 20 is formed with a attaching member 30 which is adapted to support a piston head member 32. The attaching member 30 includes a stem portion 34, a flange 36 and a pilot portion 38 all of which are formed integrally to each other at one end of the plunger assembly 20.

Thus far the syringe 10 which has been described is generally conventional except for the piston head portion 32 and is of a type commonly used in the medical field. Such syringes are considered to be disposable and are typically discarded after a single use although they are sufficiently durable to be employed more than one time.

The piston head assembly 32 is made of an elastomeric, rubber like material. As seen in FIG. 1, the lower end of the piston head member 32 is provided with a cavity 40, the walls of which conform generally to the shape of the attaching portion 30 at the end of the plunger 20. The piston head member 32 deflects sufficiently so that the attaching portion 30 may be inserted in the cavity 40 and when the attached piston head 32 is disposed in the bore 28 of the cylinder 12, radial distortion of the cylinder head 32 is restricted and the attaching portion 30 is retained securely in the cavity 40.

The upper portion of the piston head member 32 as seen in the drawings is provided with a chamber or compartment 44. The chamber 44 is closed from the internal bore 28 of the cylinder 12 by a wall element 46 which preferably is made of a relatively rigid material. The wall member 46 is held in position in an internal annular groove 48 formed in the piston head member 32 at one side of the cavity 44. The peripheral edges of the movable wall 36 are beveled as indicated at 50 to act as a cam or guide to deflect the edges of the groove 48 and permit relatively easy axial displacement of the wall element 46 relative to the piston head member 32.

The outer portion of the piston head member 32 is formed with annular seal portions 52, 54 and 56 which are adapted to engage the interior wall 28 of the cylinder 12 and act as seals preventing fluid passage from within the bore 28 and around the piston head member 32.

The compartment 44 is intended to be partially filled with an accurately measured amount of powdered material indicated at 58 and when the piston head 32 is in one end of the barrel 12, the bore 28 forms another chamber 60 in which a liquid solvent for the powdered material is introduced in a carefully measured quantity and stored until the time for mixing with powder 58.

Sterility against contaminants is very important in hypodermically injected medications and as a consequence the present mixing syringe is assembled under such sterile conditions. The cavity 44 in the piston head 32 is loaded with a carefully measured amount of powdered material after which the wall 46 is inserted to close the chamber 44 and the plunger assembly 20 together with the piston head 32 is inserted into the cylinder 12. Thereafter liquid solvent or solution may be loaded through the opening in the needle adapter 14 to the chamber 60 after which the cap 16 may be placed in position. The mixing syringe 10 may then be stored until it is used.

To use the mixing syringe 10 it simply is necessary to depress the plunger 20 by placing the cylinder 12 between two of the fingers of one hand and press on the plunger thumb rest 29. Since the cavity 44 is not completely filled with powder, movement of the piston head 32 into the cylinder bore 28 causes an increase in pressure in the chamber 60 formed in the barrel 12 and the pressure differential acting on the wall 46 causes it to be displaced into the chamber 44. Upon displacement of the wall 46 the powder and liquid is free to mix. After the complete mixing of the two materials within the mixing syringe, the cap 16 may be removed and replaced with a hypodermic needle or tube for injection or dispensing.

Referring now to FIGS. 3 and 4 illustrating another embodiment of the invention, the syringe is designated at 70 and includes the cylinder barrel 12 which is identical to that shown in FIGS. 1 and 2 embodiment. However, the plunger assembly 20' differs from the plunger assembly 20 in that a push rod 74 is supported for sliding movement longitudinally of the plunger 20' in an axially extending bore 75. The rod 74 is longer than the plunger assembly 20' and extends from its opposite ends. The rod 74 projects through the attaching member 30' and through an opening 76 in the piston head member. The piston head member 32' has a wall element 46' seated in an annular groove 48'. In this instance the beveled portion 50' faces in the opposite direction from surface 50 shown in FIG. 1. The rod 74 is provided with a finger pad 78 for moving the rod 74 axially in bore 75 and relative to the remainder of the plunger assembly 20'. When the rod 74 is so moved, the inner end 80 engages the wall 46' and displaces it and separates it from the piston head member 32' so that the chamber 44' is open to the chamber 60' formed in the barrel 12. The cam surfaces 50' facilitate dislodging wall 46' from the groove 48'.

Referring to FIG. 5 the piston head member 32' is shown prior to its assembly into the syringe 10'. The opening 76 is provided with a membrane or diaphragm 82 of thin material which is molded with the remainder of the piston head member 32' and serves to retain powdered material in the chamber 44.

To assemble the syringe shown in FIGS. 3 and 4, the head member 32' is attached to the attachment portion 30' on the plunger 20' and the attached piston head 32' is inserted into the bore 28' of the barrel. Thereafter, the rod 74 may be inserted in the axial bore 75. Just prior to use, the rod 74 is displaced relative to the plunger to pierce the membrane 82 so that the end of the rod enters the chamber 44'. To initiate mixing, the wall is displaced by the end 80 of the rod. After a thorough mixing of the powder and liquid the cap 16 may be removed from the needle adapter 14 and the latter may be connected to a hypodermic needle or hose. Thereafter, the plunger 20' as well as the rod 74 are moved simultaneously in the barrel so that the liquid mixture may be displaced from the syringe. During such displacement the liquid is prevented from leaking around the rod 74 by the resilient piston head member 32 and particularly a flange portion 84 around the opening 82 which is smaller than the diameter of the rod 74. As a result, the flange 84 forms a seal means engageable in fluid tight relationship with the outer surface of rod 74. The surfaces of piston head member 32 pressing against the flange also act to seal liquid from passing through the opening 75.

The use of the embodiments shown in FIGS. 3 and 4 is substantially the same as that of the embodiment shown in FIG. 1. With the FIG. 3 embodiment, the rod 74 is used to pierce the membrane 82 and subsequently to displace the wall member so that the chambers 44' and 60' communicate with each other for mixing of the powdered material and diluent. After sufficient mixing, the syringe 10 is provided with a hypodermic needle or other fluid connection and the liquid mixture may be displaced from the syringe in the usual manner. In other words, by holding the syringe in one hand with fingers engaged with diametrically opposed flanges 22, the thumb may be placed on the rests 78 and the rod 74 and plunger 20' are moved simultaneously so that the piston head 32' displaces the liquid from the bore 28'.

In both embodiments the attaching portions 30 and 30' of the plunger assemblies 20 and 20' prevent radial inward deflection of the annular seals 54 and 56 or 54' and 56' to insure that the seals remain in engagement with the walls of bore 28 in the cylinder 12. Similarly, the displaceable walls 46 and 46' are seated in their respective grooves 48 and 48' to resist radial inward deflection of the annular seal portions 52 or 52' to insure good sealing contact between the walls of bore 28 and the seal surfaces. Also in both embodiments, the cam surfaces 50 and 50' permit relatively easy displacement of the wall elements 46 and 46'.

Figure 6:
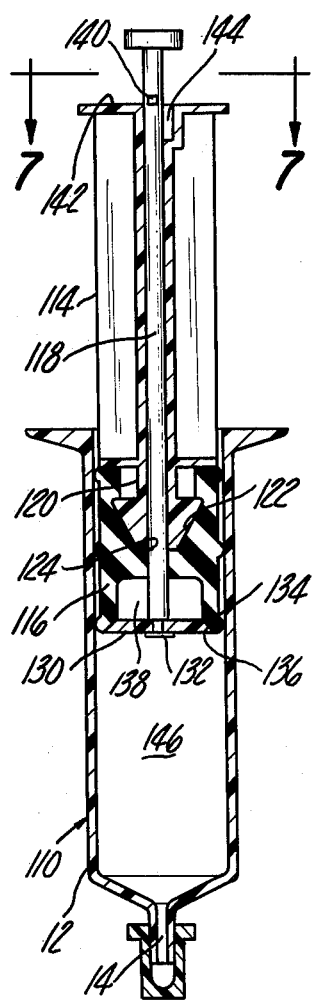
FIG. 6 is a longitudinal sectional view of another embodiment of the invention.

Another embodiment of the invention is seen in FIGS. 6 and 7 in which a syringe 110 includes a cylinder barrel 12 identical to that of the other embodiments of the invention. The plunger assembly 114, however, includes a cylinder head 116 of resilient material and an actuating rod 118. The plunger 114 has an attaching portion 120 which is received in a cavity 122 to secure the resilient piston head 116 in position in much the same manner as the earlier disclosed embodiments of the invention. The actuating rod 118 is slidably mounted within the plunger assembly 114 so that it may be moved axially thereof. The actuating rod 118 passes through an opening 124 in the piston head 116 and the end is provided with a rigid disc member 130 which is fixed to the end of the actuating rod 118 by a head portion 132. The peripheral edge of the disc 130 is provided with a bevel surface 134 which in the position shown in FIG. 6 is in engagement with an annular, bevel lip 136. With the complementary annular beveled surfaces 134 and 136 in engagement with each other the ridid disc 130 and the piston head 116 form a compartment 138.

The end of the actuating rod 118 opposite to the disc 130 projects beyond the end of the plunger 114 and is provided with a lock element 140 which projects to one side of the actuating rod 118. In FIG. 6, the lock element 140 would be in engagement with a lock surface 142 at the end of the plunger 114. Upon rotation of the actuating rod 118 approximately 90° in a counterclockwise direction was viewed in FIG. 7, the lock element 140 is brought into alignment with a recess 144 which permits the actuating rod 118 to be moved axially relative to the plunger 114 a limited amount. As a result the disc 130 is moved out of engagement with the piston head 116 to permit the compartment 138 to communicate with the chamber 146 as seen in FIG. 8 so that materials in the compartment or recess 144 can be mixed with the materials in the chamber 146.

In the position shown in FIG. 6 the lock element 140 retains the disc 130 in sealing engagement with the piston head 116 so that the chambers 144 and 146 are isolated from each other and the materials in the respective chambers are maintained separately. Also, the sealing surface 136 which is resilient, acts to resiliently bias the lock element 140 into engagement with the complementary lock surface to resist relative rotation of the plunger and actuating rod.

Figure 8:
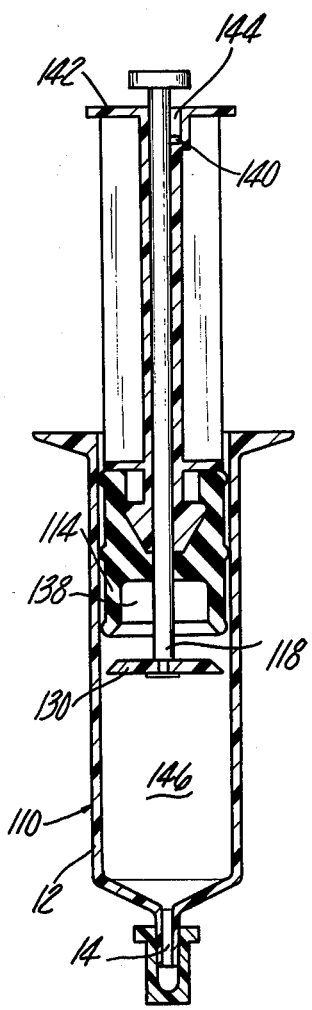
FIG. 8 is a view similar to FIG. 6 but showing another operating position of the syringe.

Just prior to use of the syringe, the actuating rod 118 is rotated to align the lock element 140 with the recess 144 after which the disc may be separated from the head 116, as seen in FIG. 8. The materials in the chambers 144 and 146 may be mixed by shaking the entire syringe and after the materials are thoroughly mixed the needle adapter 14 may be fitted with a hypodermic needle or other fitting for conveying the liquid mixture from the mixing syringe 110.

If desired, after the materials in the compartments 144 and 146 are thoroughly mixed the syringe may be held in a generally vertical position with the outlet end 14 downwardly so that the liquid mixture occupies the lower part of the barrel 12. Thereafter, the disc 130 may be pulled into sealing engagement with the head 116 by pulling the actuating rod 118 upwardly and rotating the lock element 140 to maintain the wall or disc 130 in closed position. Thereafter, application of pressure on the end of the actuating rod will serve to move the plunger and eject the liquid mixture from the discharge opening 14. This method makes it possible to eject a maximum amount of the content of the syringe.

Figure 9:
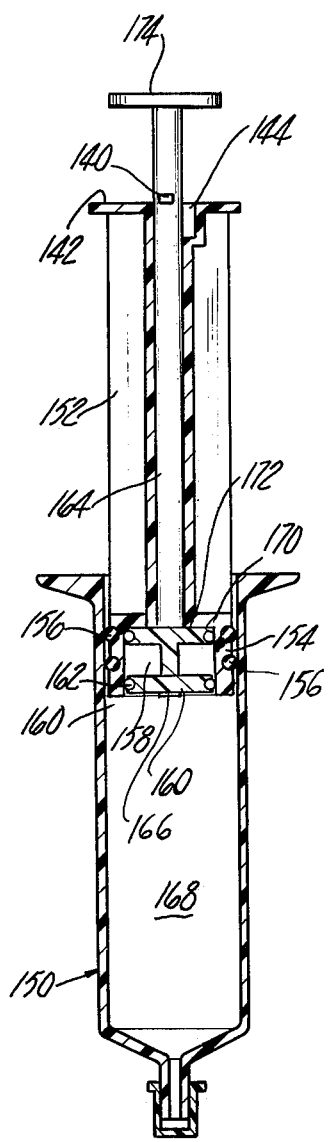
FIG. 9 is a sectional view of still another embodiment of the invention.

Another embodiment of the invention is shown in FIG. 9 in which a syringe 150 incorporates a barrel 12 identical with the barrel of the prior embodiments. The plunger assembly 152 is slidably disposed in the bore of the barrel 12. The end of the plunger 152 within the barrel is provided with a head portion 154 made of plastic and can be molded integrally with the remainder of the plunger or can be molded separately and attached by cement. The exterior of the head 154 is fitted with a pair of O-rings 156 that sealingly engage the internal walls of the bore of barrel 12 and the interior of the piston portion 154 forms a cavity or chamber 158 which is closed by a disc 160 which also is made of relatively rigid plastic material. The outer circumference of the disc 160 is provided with an O-ring seal element 162 of resilient, elastomeric material. The disc 160 and O-ring 162 are held on a stepped shoulder of an actuating rod 164 by a head portion 166. In the position shown in the drawings, the O-ring 162 engages an internal annular surface 167 in the plunger cavity 158 and serves as a seal which maintains the cavity 158 separate from the chamber 168.

Disposed within the chamber 158 and mounted on the actuating rod 164 is a wall member 170. The wall 170 includes an O-ring 172 which serves as a seal. The wall 170 may be secured to the actuator rod 164 by adhesive or the like.

The outer end of the actuating rod 164 is provided with a head 174 and like the embodiment shown in FIG. 6, with a lock element 140 which in the locked position is in engagement with the lock surface 142 and in the unlocked position is free to move in a recess 144.

In use and just prior to mixing materials in the chambers 158 and 168, the actuating rod 164 is rotated so that the lock element 140 is brought into alignment with the recess 144. Thereafter the rod 164 may be moved axially relative to the plunger 152 and the chambers 158 and 168 are opened to each other so that materials in the chambers may be mixed together. After sufficient mixing, pushing on the head 174 of the actuating rod 164 will cause the plunger 152 to move in the barrel 12 so that the mixture may be ejected from the outlet 14. During movement of the plunger 152 the O-ring 172 engages the inner wall of the plunger cavity 158 and prevents seepage of liquid but also acts to wipe the walls of the cavity 158 and insures that all material is ejected into chamber 168.

As in the case of the embodiment seen in FIG. 6, after the materials are mixed together the liquid mixture may be permitted to occupy the outlet end of the barrel 12 and the disc 160 may be moved into sealing engagement with the plunger 152. The O-ring 162 will maintain liquid mixture in the plunger 168 until it is completely ejected from the barrel 12.

A mixing syringe has been provided in which two different materials may be stored and maintained separately from each other until just prior to intended use at which time the two materials may be mixed together. One of the materials is stored in the chamber formed by the syringe barrel and plunger and the other material is stored in a chamber formed in the piston head end of the plunger. A rigid, movable wall acts to separate the two chambers from each other. In one embodiment, the wall separating the two materials is displaced upon movement of the plunger in the syringe barrel and in the other embodiments an auxiliary plunger is provided to mechanically displace the wall to place the two chambers in communication with each other.

The embodiments of the invention in which an exclusive property or privilege is claimed are defined as follows:

1. A syringe assembly for storing two different materials separately in readiness for mixing together and for injection as a liquid at the time of use, the combination of; a cylinder, a discharge port formed in a wall of said cylinder for communication with the interior of said cylinder, a plunger slidably disposed in said cylinder and projecting from an open end thereof opposite to said discharge port, said plunger forming a first chamber therein, a second chamber formed in said cylinder between said plunger and said discharge port, a movable wall member separating said first and said second chambers from each other, said second chamber being adapted to contain one of the materials to be mixed and said first chamber being adapted to contain the other of said materials, an actuating member supported for axial movement relative to said plunger, one end of said actuating member being connected to said wall and being operative to move said wall to a position communicating said first and said second chambers with each other, said plunger being movable toward said discharge port to displace said mixed materials from said cylinder and lock means for holding said rigid wall member in closed relationship with said plunger during movement of the latter to maintain said first and second chambers isolated from each other.

2. The combination of claim 1 in which said lock means includes a lock element on said actuating member engageable with a lock portion on said plunger for preventing relative movement of said plunger and actuating member when said lock element and portion are in locked position, said actuating member being movable a limited amount relative to said plunger when said lock element and portion are in their unlocked position to permit communication of said first and second chambers.

3. The combination of claim 1 and further comprising seal means between said wall member and said plunger, said seal means biasing said actuating member and plunger relative to each other to maintain said lock means in locked position.

4. The combination of claim 2 wherein said lock element is movable into engagement with a stop portion on said plunger when said lock element and lock portion are in their unlocked position to move said actuating member and plunger as a unit in one direction in response to movement of said plunger.

* * * * *

UNITED STATES PATENT AND TRADEMARK OFFICE
CERTIFICATE OF CORRECTION

PATENT NO. : 4,116,240
DATED : September 26, 1978
INVENTOR(S) : Dr. Aeneas Guiney It is certified that error appears in the above-identified patent and that said Letters Patent are hereby corrected as shown below:

Column 5, line 21, "was" should read --as--

Signed and Sealed this

Twentieth Day of March 1979

[SEAL]

Attest:

RUTH C. MASON
Attesting Officer

DONALD W. BANNER
Commissioner of Patents and Trademarks